United States Patent [19]

Lowe, III

[11] Patent Number: 4,797,403
[45] Date of Patent: Jan. 10, 1989

[54] QUINAZOLINEDIONES AND PYRIDOPYRIMIDINEDIONES

[75] Inventor: John A. Lowe, III, Stonington, Conn.

[73] Assignee: Pfizer Inc., New York, N.Y.

[21] Appl. No.: 76,976

[22] Filed: Jul. 23, 1987

Related U.S. Application Data

[63] Continuation-in-part of Ser. No. 1,718, Aug. 21, 1986.

[51] Int. Cl.$^4$ ............... C07D 293/96; C07D 471/04; A61K 31/505
[52] U.S. Cl. ............................. 514/259; 514/258; 544/285; 546/310; 548/253; 548/254; 560/43
[58] Field of Search ............ 544/285, 309; 514/259

[56] References Cited

U.S. PATENT DOCUMENTS

| | | | |
|---|---|---|---|
| 3,755,581 | 8/1973 | Janiak | 514/259 |
| 3,794,643 | 2/1974 | Yabuuchi et al. | 544/285 |
| 3,912,736 | 10/1975 | Noda et al. | 544/279 |
| 3,922,275 | 11/1975 | Noda et al. | 544/279 |
| 3,984,415 | 10/1976 | Noda et al. | 544/279 |
| 4,266,056 | 5/1981 | Henrick et al. | 544/309 |
| 4,734,419 | 3/1988 | Hashimoto et al. | 544/285 |
| 4,746,352 | 5/1988 | Wenger et al. | 544/285 |

FOREIGN PATENT DOCUMENTS

2334266  1/1974  Fed. Rep. of Germany .

OTHER PUBLICATIONS

Moore et al., J. Org. Chem., 34, pp. 887–892 (1969).

*Primary Examiner*—Donald G. Daus
*Assistant Examiner*—E. Bernhardt
*Attorney, Agent, or Firm*—Peter C. Richardson; Lawrence C. Akers; Gezina Holtrust

[57] ABSTRACT

1-Phenylquinazoline-1H,3H-2,4-diones and 1-phenyl-pyrido-[2,3d]-pyrimidine-1H,3H-2,4-diones, their esters and acid addition salts, and pharmaceutical compositions containing such compounds have antidepressant, anti-inflammatory and analgesic activity.

7 Claims, No Drawings

QUINAZOLINEDIONES AND PYRIDOPYRIMIDINEDIONES

CROSS REFERENCE TO RELATED APPLICATION

This application is a continuation in part of Ser. No. 001,718 filed Aug. 21, 1986.

BACKGROUND OF THE INVENTION

This invention relates to 1-phenylquinazoline-1H,3H-2,4-diones and 1-phenylpyrido-[2,3d]-pyrimidine-1H,3H-2,4-diones which may be 3-substituted by alkyl or substituted alkyl, pharmaceutical compositions containing such compounds as active ingredients and a method of treatment with such compounds.

U.S. Pat. Nos. 3,912,736 and 3,984,415 describe pyridopyrimidines of the formula

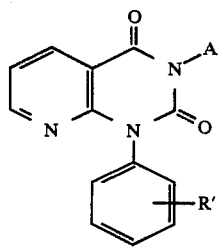

wherein A may be hydrogen, alkyl or aralkyl and R' may be nitro, halogen, trifluoromethyl and other substituents. German patent publication No. 2334266 has a similar disclosure. Similar quinazoline compounds are known from U.S. Pat. Nos. 3,794,643 and 4,016,166. The compounds are disclosed as having central nervous system depressive, analgesic and antiinflammatory activities.

SUMMARY OF THE INVENTION

The compounds of the invention are quinazoline-1H,3H-2,4-diones and pyrido-[2,3d]-pyrimidine-1H,3H-2,4-diones of the formula

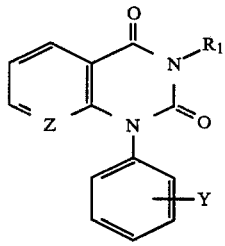

I or a pharmaceutically acceptable acid addition salt thereof, wherein $R_1$ is hydrogen, alkyl of 1 to 3 carbon atoms, cyclopentylmethyl, cyclohexylmethyl, norbornylmethyl, [2.2.2]bicyclooctylmethyl, or benzyl, the phenyl of the benzyl optionally being substituted by halogen, trifluoromethyl, nitro, carboxy, or $CO_2M$ wherein M is a pharmaceutically acceptable cation; Y is carboxy, carboalkoxy wherein the alkoxy has 1 to 6 carbon atoms, carbobenzyloxy, carboxamido, N-alkyl carboxamido wherein the alkyl has 1 to 6 carbon atoms, or $CO_2M$ wherein M is as defined above, and Z is N or CH, provided that when Z is CH, then $R_1$ is benzyl and Y includes tetrazole optionally substituted by alkyl of 1 to 3 carbon atoms or benzyl.

When Z is N, Y may be substituted in the meta or para position of the 1-phenyl group. When Z is CH, Y is meta-substituted. When $R_1$ is substituted benzyl, the substitution is at the meta and/or para positions.

Specific compounds of the invention are those wherein $R_1$ is benzyl, Z is N or CH and Y is N-methylcarboxamido or carbomethoxy.

The invention includes pharmaceutical compositions comprising a compound of formula I, wherein $R_1$, Y and Z are as defined above, in an amount effective in the treatment of depression, inflammations such as psoriasis, or asthma, or in an analgesically effective amount, and a pharmaceutically acceptable carrier or diluent.

The invention further includes a method of treating depression, inflammations such as psoriasis, or asthma, or a method of inducing analgesia by administering to a subject in need of such treatment or inducement an amount of a compound of formula I effective in such treatment or inducement, wherein $R_1$, Y and Z are as defined above.

DETAILED DESCRIPTION OF THE INVENTION

The compounds of formula I wherein $R_1$ is as defined above, except $R_1$ is not benzyl substituted by carboxy, and Y is as defined above may be prepared by reacting, in the presence of an acid catalyst, a compound of the formula

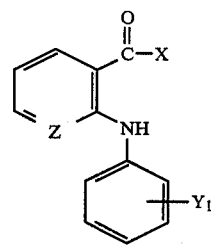

wherein X is alkoxy of 1 to 6 carbon atoms and $Y_1$ is Y except for carboxy, with a compound of the formula $$R_1N=C=O \qquad III$$

wherein $R_1$ is as defined above except that when $R_1$ is carboxy-substituted benzyl, the carboxy group is a protected group such as an ester group which is subsequently hydrolyzed to release the carboxy group.

The cyclization reaction is conveniently carried out in an organic solvent such as dimethylformamide, diglyme, tetrahydrofuran or alcohol, in the presence of an acid catalyst such as hydrogen chloride. The reaction temperature is not critical, and may be ambient or higher, e.g. up to about 200° C. However, preferably, the reaction is at the reflux temperature of the solvent used.

The carboxylic acid (I) wherein Y is carboxy may be prepared from corresponding compounds wherein Y is carboalkoxy by conventional hydrolysis such as in ethanolic base. The base may be potassium hydroxide.

The compound (I) wherein $R_1$ is benzyl substituted by carboxy is prepared from the corresponding compound (I) wherein $R_1$ is a protected group such as a carboalkoxy, wherein the alkoxy has 1 to 6 carbon atoms, by conventional hydrolysis as described above.

The compound (I) wherein Y is carbobenzyloxy may be prepared by transesterification of compound (I) wherein Y is carboalkoxy with benzylalcohol in the presence of a catalyst such as an acid or base.

The amide (I) wherein Y is carboxamido or N-alkylcarboxamido may be prepared by reacting the corresponding carboxylic acid (I) with ammonia or an alkylamine, respectively, wherein the alkyl in the alkylamine contains from 1 to 6 carbon atoms.

The compounds of formula II are prepared by reacting 2-chloronicotinic acid with 3-aminobenzoic acid in an inert atmosphere such as nitrogen. The reaction is usually carried out in an organic solvent such as dimethyl formamide, diglyme, tetrahydrofuran or an alcohol. Preferably, a metallic compound is present such as copper powder or copper bromide, and an inorganic base such as alkali metal carbonate or hydroxide, or an organic base such as trialkylamine, or pyridine. The reaction temperature is not critical and may be ambient or elevated up to about 150° C. Preferably, the reaction is carried out at the reflux temperature of the organic solvent used.

The isocyanate $R_1N=C=O$ wherein $R_1$ is as defined above in connection with formula I except that $R_1$ is not benzyl substituted by carboxy may be formed by reaction of diphenylphosphoryl azide with a compound of formula $R_1COOH$, wherein $R_1$ is as defined immediately above in connection with $R_1NCO$, in the presence of a weak base such as a tertiary amine, e.g. triethylamine.

The formation of the isocyanate is preferably done in situ without isolation of the isocyanate before the subsequent cyclization to compounds of formula I as described above. The solvents for the in situ formation of the isocyanate and the subsequent cyclization must be inert under the reaction conditions of both the isocyanate formation and the cyclization. Suitable solvents are higher boiling hydrocarbons, such as xylene or chlorobenzene having boiling points of about 130° to 140°, and other organic solvents such as dimethylformamide, and diglyme.

Alternative general methods which can be adapted to make novel compounds (I) are described in the prior art such as above mentioned U.S. Pat. No. 3,984,415, the disclosure of which is hereby incorporated by reference, and British Pat. No. 1,484,293.

The pharmaceutically acceptable cation salts of the compounds of formula I may be prepared by conventional methods. For instance, the salts may be prepared by treating the compound of formula I in which $R_1$ is carboxybenzyl or Y is carboxy with an aqueous solution of the desired pharmaceutically acceptable cation in the hydroxide form in equivalent amounts, and evaporating the resulting solution to dryness, preferably under reduced pressure. Suitable pharmaceutically acceptable cation hydroxides for this purpose include alkali metal hydroxides such as potassium, sodium and lithium hydroxides, alkaline earth metal hydroxides such as calcium and magnesium hydroxide. Alternatively, the salts may be prepared by reaction of compound (I) in which Y is carboxy with ammonia or organic amines, such as diethanolamine and N-methylglucamine.

The pharmaceutically acceptable acid addition salts of the compounds of formula I wherein Z is N are prepared in a conventional manner by treating a solution or suspension of the free base (I) with about one chemical equivalent of a pharmaceutically acceptable acid. Conventional concentration and recrystallization techniques are employed in isolating the salts. Illustrative of suitable acids are sulfuric, phosphoric, hydrochloric, hydrobromic, hydroiodic, sulfamic, sulfonic such as methanesulfonic, benzenesulfonic, trifluoromethanesulfonic and related acids. Preferably, the acid is methanesulfonic acid.

The compounds of the invention can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules either alone or in admixture with excipients, or in the form of elixirs or suspensions containing flavoring or coloring agents. They can be injected parenterally, for example, intramuscularly, intravenously or subcutaneously. For parenteral administration, they are best used in the form of a sterile aqueous solution which can contain other solutes, for example, enough salt or glucose to make the solution isotonic. Generally, compound (I) is dissolved in a pharmaceutically acceptable liquid such as water which may contain buffers, preservatives, materials to make the solution isotonic, e.g. isotonic saline, or other materials known to those skilled in the art. The reconstituted solution so prepared may be added to a solution such as an I.V. solution for slow administration by infusion.

The invention also provides pharmaceutical compositions comprising an antidepressant, anti-inflammatory, anti-asthmatic or an analgesically effective amount of the compound of formula I together with a pharmaceutically acceptable diluent or carrier.

The compounds of the invention can be administered to subjects for the treatment of depression, inflammations, or asthmatic conditions, or for inducement of analgesia by either the oral or parenteral routes, and may be administered at dosage levels of about 0.1 to 30 mg/kg/day, advantageously 0.5–20 mg/kg/day. Variations will necessarily occur depending on the weight and condition of the subject being treated and the particular route of administration chosen as will be known to those skilled in the art.

The invention yet further provides a method of treating a subject in need of treatment for depression, inflammation or asthma, or inducement of analgesia by administering an effective amount of a compound of the formula (I) or a pharmaceutical composition as defined above.

The antidepressant activity of the compounds of the invention is determined by standard pharmacological tests including the behavioral despair paradigm described by R. D. Porsolt in Arch. Int. Pharmacodyn. 227, 327(1977). The procedure comprises administering the compound to a mouse (Male CD (Charles River), weighing 20–25 g) which is then placed in a plexiglass cylinder (25 cm high and 10 cm in diameter) containing 6 cm water of 25° C. one hour after injection. The mouse is left in the cylinder for 6 minutes and after the first two minutes observed for duration of mobility.

The antiinflammatory activity is determined by the platelet-activity factor (PAF) lethality test described by J. M. Young et al in Prostaglandins, 30, 545 (1985). The procedure comprises administering orally to mice 0.1 ml/10 g body weight of the compound tested. The mice are then 35 to 40 minutes later placed under a heat lamp to dilate the caudal vein for PAF injection intravenously at 0.1 ml/10 g of body weight. After injection, death follows usually within about 30 minutes, rarely after 60 minutes. The test results are expressed in percent mortality compared to controls.

The following Examples illustrate the invention. All temperatures are in degrees centigrade.

EXAMPLE 1

A. Methyl 2-(3-carbomethoxphenylamino)-nicotinate

To a 500 ml round-bottomed flask equipped with condenser and $N_2$ inlet were added 15.7 g (0.10 mol) of 2-chloronicotinic acid, 19.9 g (0.145 mol) of 3-aminobenzoic acid, 34.5 g (0.25 mol) of potassium carbonate, 30 mg of copper powder, and 40 ml of dimethylformamide. The mixture was heated to reflux and 150 mg of methanol-washed copper(I) bromide was added in three portions over 10 minutes. The reaction turned dark and partially solidified as it was refluxed for 4.5 hours. It was then cooled, taken up in 1 liter 1N HCl, the pH adjusted to 3.5, and filtered to remove copper and dark, tarry impurities. The filtrate was adjusted to pH 2.5, saturated with sodium chloride, stirred for 3 hours, and the precipitate filtered, washed with a minimal amount of water, and dried.

The resulting solid was taken up in 500 ml dry methanol, saturated with hydrogen chloride gas, and heated at reflux for 2.5 days. The reaction was cooled, filtered from some residual sodium chloride from the previous step, and evaporated. The residue was taken up in excess aqueous saturated sodium bicarbonate solution, stirred and the aqueous layer decanted off the resulting gummy precipitate. The precipitate was chromatographed on silica gel using 5% ethyl acetate in methylene chloride as eluent to afford a light yellow oil, which crystallized on standing, mp 105°–106° C.

B. 1-(3-Carbomethoxyphenyl)-3-benzyl-pyrido-[2,3d]-pyrimidine-1H,3H-2,4-dione

To a 65 ml round-bottomed flask equipped with condenser and $N_2$ inlet were added 2.22 g (7.76 mmol) of methyl 2-(3-carbomethoxyphenylamino)-nicotinate, 3 ml dry xylene, 0.96 ml (7.76 mmol) of benzyl isocyanate, and 3 mg of camphorsulfonic acid. The reaction was heated to reflux for 6 days, cooled, evaporated, and the residue chromatographed on silica gel using 3% ethyl acetate in methylene chloride to elute unreacted diester and 10% ethyl acetate in methylene chloride to elute the product, which was triturated with ether to a white solid, mp 157°–160° C., 938 mg (31.2% yield).

EXAMPLE 2

1-(3-Benzyloxycarbonylphenyl)-3-benzyl-pyrido-[2,3d]-pyrimidine-1H,3H-2,4-dione

To a 35 ml round-bottomed flask equipped with condenser and $N_2$ inlet were added 0.30 g (0.77 mmol) of 1-(3-methoxycarbonylphenyl)-3-benzyl-pyrido-[2,3d]-pyrimidine-1H,3H-2,4-dione, 8 ml of benzyl alcohol, and 10 mg of camphorsulfonic acid. The reaction was heated at reflux for 48 hours, cooled, and chromatographed on silica gel using ether/hexane. The product fractions were combined and triturated with ether to give 32 mg (9.0% yield) of white crystalline solid, mp 160°–162° C.

EXAMPLE 3

1-(3-Carboxyphenyl)-3-benzyl-pyrido-[2,3d]-pyrimidine-1H,3H-2,4-dione

To a 35 ml round-bottomed flask equipped with condenser and $N_2$ inlet were added 100 mg (0.26 mmol) of 1-(3-carbomethoxyphenyl)-3-benzyl-pyrido-[2,3d]-pyrimidine-1H,3H-2,4-dione, 15 mg (0.26 mmol) of sodium chloride, 9 mg (0.52 mmol) of water, and 1.5 ml of dimethylsulfoxide. The reaction was heated at reflux for 3 days, cooled, diluted with water, and extracted into ethyl acetate. The organic layer was dried over magnesium sulfate, filtered, and evaporated. The resulting oil was chromatographed on silica gel using methylene chloride/methanol as eluent, and product fractions combined and evaporated. The resulting solid was triturated with pentane/ethyl ether to afford an off-white solid, mp 248°–250° C., 4 mg.

EXAMPLE 4

1-(3-Carboethoxyphenyl)-3-benzyl-pyrido-[2,3d]-pyrimidine-1H,3H-2,4-dione

To a 35 ml round-bottomed flask equipped with condenser and $N_2$ inlet were added 600 mg (1.91 mmol) of ethyl 2-(3-carboethoxyphenlyamino)nicotinate (prepared as in Example 1A but using ethanol in place of methanol), 1 ml dry dimethylformamide, 0.25 g (1.91 mmol) of benzyl isocyanate, and 10 mg camphorsulfonic acid. The reaction was heated at reflux for 24 hours, cooled, taken up in ethyl acetate, washed with water, dried over magnesium sulfate, and evaporated to an oil. The oil was chromatographed on silica gel using ethyl acetate/methylene chloride as eluent to give a white crystalline solid, mp 171°–174° C., 70 mg.

EXAMPLE 5

1-(3-Carboisopropoxyphenyl)-3-benzyl-pyrido-[2,3d]-pyrimidine-1H,3H-2,4-dione

To a 35 ml round-bottomed flask equipped with condenser and $N_2$ inlet were added 690 mg (2.02 mmol) of ethyl 2-(3-carboisopropoxyphenylamino)nicotinate (prepared as in Example 1A but using isopropanol in place of methanol), 1 ml dry dimethylformamide, 0.27 g (2.02 mmol) of benzyl isocyanate, and 10 mg camphorsulfonic acid. The reaction was heated at reflux for 24 hours, cooled, taken up in ethyl acetate, washed with water, dried over magnesium sulfate, and evaporated to an oil. The oil was chromatographed on silica gel using ethyl acetate/methylene chloride as eluent to give a white crystalline solid, mp 205°–207° C., 79 mg.

EXAMPLE 6

1-(3-Carbomethoxyphenyl-3-(4-fluoro-benzyl)-pyrido[2,3d]-pyrimidine-1H,3H-2,4-dione To a 35 ml round-bottomed flask equipped with condenser and $N_2$ inlet were added 1.0 g (3.496 mmol) of methyl 2-(3-carbomethoxyphenylamino)-nicotinate, 0.54 g (3.496 mmol) of 4-fluorophenyl acetic acid, 4 ml of dry xylene, 0.83 ml (3.846 mmol) of diphenylphosphoryl azide, and 0.54 ml (3.846 mmol) of triethyl amine. The reaction was heated to 70° C., whereupon a gas was evolved, and 5 mg camphorsulfonic acid was added once gas evolution had ceased. The reaction was heated at reflux for 2.5 days, cooled, and chromatographed on silica gel using ethyl acetate in methylene chloride as eluent to give 70 mg (4.9% yield) of a white solid, mp 172°–175° C.

EXAMPLE 7

1-(3-Carbomethoxphenyl)-3-(4-chloro-benzyl)-pyrido[2,3d]-pyrimidine-1H,3H-2,4-dione To a 35 ml round-bottomed flask equipped with condenser and $N_2$ inlet were added 1.0 g (3.496 mmol) of methyl 2-(3-carbomethoxyphenylamino)-nicotinate, 0.60 g (3.496 mmol) of 4-fluorophenyl acetic acid, 4 ml of dry xylene, 0.83 ml (3.846 mmol) of diphenylphosphoryl azide, and 0.54 ml (3.846 mmol) of triethyl amine. The reaction was heated to 70° C., whereupon a gas was evolved, and 5 mg camphorsulfonic acid was added once gas evolution had ceased. The reaction was heated at reflux for 2.5 days, cooled, and chromatographed on silica gel using ethyl acetate in methylene chloride as eluent to give 32 mg (2.2% yield) of a white solid, mp 120°–130° C. NMR (DMSO-$d_6$): 3.87 (3H, s), 5.15 (2H, s), 7.1–8.5 (11H, m).

EXAMPLE 8

1-(3-Carbomethoxphenyl)-3-(cyclopentylmethyl)-pyrido[2,3d]-pyrimidine-1H,3H-2,4-dione To a 35 ml round-bottomed flask equipped with condenser and $N_2$ inlet were added 1.0 g (3.496 mmol) of methyl 2-(3-carbomethoxyphenylamino)-nicotinate, 0.44 g (3.496 mmol) of cyclopentyl acetic acid, 4 ml of dry xylene, 0.83 ml (3.846 mmol) of diphenylphosphoryl azide, and 0.54 ml (3.846 mmol) of triethyl amine. The reaction was heated to 70° C., whereupon a gas was evolved, and 5 mg camphorsulfonic acid was added once gas evolution had ceased. The reaction was heated at reflux for 2.5 days, cooled, and chromatographed on silica gel using ethyl acetate in methylene chloride as eluent to give 67 mg (5.1% yield) of a white solid, mp 149°–151° C.

EXAMPLE 9

1-(3-Carbomethoxphenyl)-3-(norbornylmethyl)-pyrido[2,3d]-pyrimidine-1H,3H-2,4-dione The title compound (281 mg of white solid, mp 157°–159° C.) was prepared as in Example 8 from 1.0 g (3.496 mmol) of methyl 2-(3-carbomethoxyphenylamino)nicotinate, 0.51 g (3.496 mmol) of norbornyl acetic acid, 4 ml of dry xylene, 0.83 ml (3.846 mmol) of diphenylphosphoryl azide, and 0.54 ml (3.846 mmol) of triethyl amine.

EXAMPLE 10

Methyl 2-(4-carbomethoxphenylamino)-nicotinate

A. The title compound (4.8 g white solid, mp 138°–139° C.) was prepared as in Example 1.A from 7.85 g (0.05 mol) of 2-chloronicotinic acid, 9.95 g (0.0725 mol) of 4-aminobenzoic acid, 17.25 g (0.125 mol) of potassium carbonate, 30 mg of copper powder, and 30 ml of dimethylformamide.

1-(4-Carbomethoxyphenyl-3-benzyl pyrido-[2,3d]-pyrimidine-1H,3H-2,4-dione

B. The title compound (582 mg white solid, mp 179°–811° C.) was prepared as in Example 1.B from 2.22 g (7.76 mmol) of methyl 2-(4-carbomethoxphenylamino)nicotinate, 3 ml dry xylene, 0.96 ml (7.76 mmol) of benzyl isocyanate, and 3 mg of camphorsulfonic acid.

EXAMPLE 11

1-(3-Carboxamidophenyl)-3-benzyl-pyrido-[2,3d]-pyrimidine-1H,3H-2,4-dione

To a 25 ml round-bottomed flask equipped with $N_2$ inlet and rubber septum were added 150 mg (0.402 mmol) of 1-(3-carboxyphenyl)-3-benzyl-pyrido-[2,3d]-pyrimidine-1H,3H-2,4-dione, 1.4 ml methylene chloride, 0.4 ml dimethylformamide, and 41 mg (0.402 mmol) of N-methyl morpholine. The reaction was cooled to −5° C. and 55 mg (0.402 mmol) of isobutylchloroformate was added, and the reaction stirred for 5 minutes. Ammonia gas was then bubbled through the reaction for 3 minutes and the reaction allowed to warm to room temperature and stirred for 2 hours. The reaction was then quenched by addition of 2N aqueous sodium hydroxide solution, and extracted into ethyl acetate. The ethyl acetate layer was washed with 2N aqueous sodium hydroxide and water, dried over magnesium sulfate, and evaporated. The residue was triturated with ether to yield a white solid, 105 mg (70% yield), mp 245°–246° C.

EXAMPLE 12

1-(3-N-methylcarboxamidophenyl)-3-benzyl-pyrido-[2,3d]-pyrimidine-1H,3H-2,4-dione To a 25 ml round-bottomed flask equipped with $N_2$ inlet and rubber septum were added 150 mg (0.402 mmol) of 1-(3-carboxphenyl)-3-benzyl--pyrido-[2,3d]-pyrimidine-1H,3H-2,4-dione, 3.0 ml methylene chloride, 0.7 ml dimethylformamide, and 41 mg (0.402 mmol) of N-methyl morpholine. The reaction was cooled to −10° C. and 55 mg (0.402 mmol) of isobutylchloroformate was added, and the reaction stirred for 5 minutes. N-Methylamine gas was then bubbled through the reaction for 2 minutes and the reaction allowed to warm to room temperature and stirred for 2 hours. The reaction was then quenched by addition of 2N aqueous sodium hydroxide solution, and extracted into ethyl acetate. The ethyl acetate layer was washed with 2N aqueous sodium hydroxide and water, dried over magnesium sulfate, and evaporated. The residue was triturated with ether to yield a white solid, 100 mg (64.5% yield), mp 252°–253° C.

EXAMPLE 13

A. Methyl 2-(3-carbomethoxyphenylamino)-benzoate

To a 500 ml round-bottomed flask equipped with condenser and $N_2$ inlet were added 15.7 g (0.10 mol) 2-chlorobenzoic acid, 23.3 g (0.17 mol) 3-aminobenzoic acid, 23.5 g (0.17 mol) potassium carbonate, 50 mg copper powder, and 40 ml dimethylformamide. The mixture was heated to reflux, and three 50 mg portions of methanol-washed copper(I) bromide were added. The reaction was refluxed 3.5 hours, cooled, and poured into 1 l 1N HCl. The mixture was stirred for 10 minutes, filtered, and the filtered solid washed with water, methanol, and ether, and dried to afford a gray solid, mp 277°–279° C., 19 g (73.9%). The acid was taken up in 250 ml methanol, the solution saturated with HCl and refluxed 40 hours, and cooled and evaporated. The residue was chromatographed on silica gel using methylene chloride as eluent to afford 17.46 g (61.3% overall) of a yellow oil. NMR (d, CDCl$_3$): 3.97 (s, 3H), 6.7–8.0 (m, 8H). IR (Cm.$^{-1}$, KBr): 1730 (C=O).

B. 1-(3-Carbomethoxyphenyl)-3-benzylquinazoline-1H,3H-2,4-dione

To a 250 ml round-bottomed flask equipped with condenser and $N_2$ inlet were added 17.46 g (61.26 mmol) methyl 2-(3-carbomethoxyphenylamino)-benzoate, 2.57 ml (61.26 mol) benzylisocyanate, 5 mg camphorsulfonic acid, and 40 ml xylene. The reaction was refluxed for 3 days, cooled, and evaporated. The residue was crystallized from ethyl acetate/isopropyl ether in two crops to afford a solid, mp 150°–151.5° C., 8.80 g (37.2%).

EXAMPLE 14

1-(3-Carboxyphenyl)-3-benzylquinazoline-1H,3H-2,4-dione

To a 500 ml round-bottomed flask equipped with condenser and N₂ inlet were added 3.86 g (10 mmol) 1-(3-carbomethoxyphenyl)-3-benzylquinazoline-1H,3H-2,4-dione, 24.1 g (180 mmol) lithium iodide, and 250 ml dimethylformamide. The reaction was refluxed 36 hours cooled, and added to 1 l 1N HCl. The mixture was stirred for 20 minutes, filtered, and the solid washed with water and dried to afford mp 260°–262° C., 3.55 g (95.4%).

EXAMPLE 15

1-(3-N-Methylcarboxamidophenyl)-3-benzylquinazoline-1H,3H-2,4-dione

To a 100 ml three-necked round-bottom flask equipped with septum and N₂ inlet were added 0.50 g (1.34 mmol) 1-(3-carboxyphenyl)-3-benzylquinazoline-1H,3H-2,4-dione, 0.15 ml (1.34 mmol) N-methylmorpholine, 10 ml methylene chloride, and 1.5 ml dimethylformamide. The solution was cooled to −10° C. and 0.17 ml (1.34 mmol) isobutyl chloroformate added. The reaction was stirred at −10° C. for 10 minutes, then methylamine gas was bubbled through the solution for 10 minutes. The reaction was allowed to warm to room temperature and stirred for 3 days. It was taken up in methylene chloride, washed with 1N HCl and brine, dried, and evaporated. The residue was chromatographed on silica gel using methylene chloride/ethyl acetate as eluent to afford 0.45 g (87.2%) of a white, crystalline solid after trituration with isopropyl ether, mp 250°–251° C.

EXAMPLE 16

A. 3-(1-Methyltetrazol-3-yl)aniline

To a 125 ml round-bottomed flask equipped with condenser and N₂ inlet were added 1.48 g (10 mmol) 3-nitrobenzonitrile, 0.053 g (1 mmol) ammonium chloride, 0.715 g (11 mmol) sodium azide, and 20 ml dimethylformamide. The reaction was heated to 100° C. for 3 hours, cooled, and evaporated. The residue was taken up in water, cooled to 0° C., and adjusted to pH 2 with 6N HCl. The precipitate was filtered and dried to a yellow solid, mp 90°–93° C., 1.5 g (78.5%).

The tetrazole was methylated as follows: To a 125 ml round-bottomed flask equipped with condenser and N₂ inlet were added 1.4 g (73.2 mmol) 3-(tetrazol-3-yl)nitrobenzene, 0.776 g (73.2 mmol) potassium carbonate, 0.455 ml (73.2 mmol) methyl iodide, and 30 ml acetone. The reaction was refluxed for 18 hours, cooled, and evaporated. The residue was partitioned between water (adjusted to pH 2) and methylene chloride, the layers separated, and the aqueous layer extracted with methylene chloride. The combined organic layers were dried over sodium sulfate and evaporated. The residue was chromatographed on silica gel using methylene chloride as eluent to afford 0.85 g (56.6%) of a yellow solid, mp 99°–101° C.

The nitro group was reduced as follows: To a 250 ml Parr bottle were added 800 mg (3.9 mmol) of 3-(1-methyltetrazol-3-yl)nitrobenzene, 200 mg platinum oxide, and 75 ml ethanol. The reaction was pressurized with 45 p.s.i. hydrogen for 1 hour, then catalyst removed by filtration, and the solvent evaporated to afford 635 mg (93.0%) of a white solid, mp 93°–95° C.

B. Methyl 2-(3-(1-methyltetrazol-3-yl)phenylamino)benzoate

To a 125 ml round-bottomed flask equipped with condenser and N₂ inlet were added 2.5 g (14.27 mmol) 3-(1-methyltetrazol-3-yl)aniline, 2.23 g (14.27 mmol) 2-chlorobenzoic acid, 4.9 g (35.6 mmol) potassium carbonate, 20 mg copper powder, and 20 ml dimethylformamide. The reaction was heated to reflux and 100 mg of methanol-washed copper (I) bromide was added in four portions over 20 minutes. The reaction was refluxed for 16 hours, cooled, and poured into 200 ml ice/water. The mixture was filtered, washed with methylene chloride. This second organic extract was evaporated to afford 800 mg (19.0%) of a solid, mp 197°–199° C.

The solid was dissolved in 50 ml methanol in a 125 ml round-bottomed flask equipped with condenser and N₂ inlet and the solution saturated with HCl gas and refluxed for 2 days. The reaction was evaporated and chromatographed on silica gel using ethyl acetate as eluent to afford 500 mg (59.7%) of a yellow solid, mp 106°–108° C.

C. 1-(3-(1-Methyltetrazol-3-yl)phenyl)-3-benzylquinazoline-1H,3H-2,4-dione

To a 10 ml round-bottomed flask equipped with condenser and N₂ inlet were added 500 mg (1.61 mmol) methyl 2-(3-(1-methyltetrazol-3-yl)phenylamino)benzoate, 0.199 ml (1.61 mmol) benzyl isocyanate, 5 mg camphorsulfonic acid, and 2 ml xylene. The reaction was refluxed for 3 days, cooled, and evaporated. The residue was chromatographed on silica gel using methylene chloride/ethyl acetate as eluent to afford 175 mg (26.5%) of a white solid, mp 234°–236° C.

I claim:

1. A compound of the formula

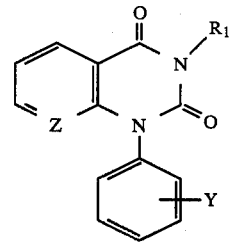

or a pharmaceutically acceptable acid addition salt thereof, wherein
   R₁ is benzyl;
   Y is carboxy, carboalkoxy wherein the alkoxy has 1 to 6 carbon atoms, carbobenzyloxy, carbamoyl, N-alkylcarbamoyl wherein the alkyl has 1 to 6 carbon atoms, CO₂M wherein M is a pharmaceutically acceptable cation, or
   Z is CH.

2. A compound according to claim 1 wherein Y is N-methylcarbamoyl.

3. A compound according to claim 1 wherein Y is carbomethoxy.

4. A composition having antidepressant activity comprising a compound according to claim 1 in an amount effective in the treatment of depression or inflammations, and a pharmaceutically acceptable carrier.

5. A composition according to claim 4 wherein and Y is N-methylcarbamoyl.

6. A composition according to claim 3 wherein Y is carbomethoxy.

7. A method of treating depression or inflammations which comprises administering to a subject in need of treatment an antidepressant or anti-inflammatory amount of a compound according to claim 1.

* * * * *

UNITED STATES PATENT AND TRADEMARK OFFICE
CERTIFICATE OF CORRECTION

PATENT NO. : 4,797,403
DATED : January 10, 1989
INVENTOR(S) : John A. Lowe, III

It is certified that error appears in the above-identified patent and that said Letters Patent is hereby corrected as shown below:

Column 10, line 50, insert before "or" the following: -- tetrazole optionally substituted by alkyl of 1 to 3 carbon atoms; --.

Signed and Sealed this

Sixteenth Day of January, 1990

*Attest:*

JEFFREY M. SAMUELS

*Attesting Officer*   Acting Commissioner of Patents and Trademarks